The United States Patent [19]

DeBonville et al.

[11] Patent Number: 5,047,345
[45] Date of Patent: * Sep. 10, 1991

[54] COMPOSITION FOR ISOLATING AND PURIFYING NUCLEIC ACID AND IMPROVED METHOD USING SAME

[75] Inventors: David A. DeBonville, Cambridge; Gerard E. Riedel, Concord, both of Mass.

[73] Assignee: Genetics Institute, Cambridge, Mass.

[*] Notice: The portion of the term of this patent subsequent to May 23, 2006 has been disclaimed.

[21] Appl. No.: 360,276

[22] Filed: Jun. 2, 1989

[30] Foreign Application Priority Data

May 22, 1989 [WO] PCT Int'l Appl. .................. PCT/US89/02234

[51] Int. Cl.$^5$ .......................... C12N 1/08; C12N 1/06; C12Q 1/68; C07H 15/12
[52] U.S. Cl. .................................. 435/270; 435/259; 435/803; 435/6; 536/27; 536/28; 536/29
[58] Field of Search ............................. 536/23, 28, 29; 435/259, 270, 803, 6

[56] References Cited

U.S. PATENT DOCUMENTS 4,833,239 5/1989 DeBonville et al. ................. 536/27
4,843,012 6/1989 DeBonville et al. ............... 435/270

Primary Examiner—Christine Nucker
Assistant Examiner—Mindy Fleisher
Attorney, Agent, or Firm—Iandiorio & Dingman

[57] ABSTRACT

A composition for isolating and purifying nucleic acid from cell culture medium and a method for isolating and purifying nucleic acid from cell culture medium employing the composition, in which the reagent includes about 1 to 3.5M acetate salt solution, about 4 to 11.2M acetic acid, about 1 to 40% by volume phenol, and about 1 to 40% by volume chloroform.

18 Claims, No Drawings

COMPOSITION FOR ISOLATING AND PURIFYING NUCLEIC ACID AND IMPROVED METHOD USING SAME

FIELD OF INVENTION

This application claims priority of identical international application PCT/US89/02234, filed on May 22, 1989.

This invention relates to a reagent composition for use in isolating and purifying nucleic acid from eukaryotic and prokaryotic cell and virus cultures, and an improved method using such composition.

BACKGROUND OF INVENTION

In the practice of biotechnology, nucleic acid fragments are commonly isolated from prokaryotic and eukaryotic and viral cultures. The isolation of these fragments enables their sequencing, their use as probes for diagnostic and other research assays, and their assembly into genes encoding whole proteins or polypeptides. Traditionally, nucleic acids have been separated from contaminating proteinaceous material (e.g., from bacterial and viral cultures) by lysis in the presence of a detergent (e.g., sodium dodecyl sulfate) and a salt solution (e.g., potassium acetate) followed by extraction (deproteinization) with phenol or chloroform or a mixture thereof. These procedures separate the nucleic acids, generally by precipitation, from lipid and protein contaminants of the cell or virus culture.

In recombinant DNA research, DNA molecules are commonly isolated from bacterial cell cultures and bacteriophage cultures. For example, double-stranded plasmid DNA is produced within and isolated from bacterial cells, e.g. *Escherichia coli*, that are cultured in liquid nutrient broth media. Bacteriophage M13 single-stranded template DNA is produced by the bacteriophage M13 propagated on an appropriate E. coli host. Template DNA is isolated from bacteriophage that have been released by host bacteria into a nutrient broth medium. The isolation of these plasmid DNA or template DNA molecules enables the sequencing thereof, and the use of the molecules for diagnostic and other assays, for their assembly into genes encoding a polypeptide of interest or for their use as vectors to produce such polypeptides.

The procedure commonly used for the isolation of plasmid DNA from bacterial cultures is described in H. C. Birnboim and J. Doly, "A Rapid Alkaline Extraction Procedure for Screening Recombinant Plasmid DNA", *Nucleic Acids Res.*, 7: 1513–1523 (1979). Template DNA is isolated in a similar manner. See, e.g., Leder et al., *Science*, 196:175 (1977). Briefly, the DNA is separated from contaminating proteinaceous material in the conditioned medium by lysis in the presence of lysozyme in a detergent and salt solution. This lysis step is followed after an incubation or neutralization step at a low temperature by extraction or deproteinization with phenol or chloroform or a mixture thereof. The nucleic acids are then separated by precipitation from lipid and other protein constituents of the culture. In non-plasmid, cosmid or phagmid DNA separation techniques, the neutralization step is typically not needed. In the procedures, lysis and deproteinization, or neutralization and deproteinization, are separately performed in two distinct steps because the reagents needed to perform the lysis or neutralization steps are not miscible with the reagents involved in deproteinization. See also: T. Maniatis et al., *Molecular Cloning—A Laboratory Manual*, Cold Spring Harbor Laboratory (1982) for a more detailed description of the specific steps of the isolation procedure.

Due to the frequency with which these DNA isolating and purifying steps are employed, and the researcher time which is consumed in performing the Maniatis et al. steps, there is a need in the art of recombinant DNA research for more efficient methods of DNA isolation.

SUMMARY OF INVENTION

It is therefore an object of this invention to provide a greatly simplified nucleic acid isolation procedure.

It is a further object of this invention to provide such an isolation procedure in which the neutralization and deproteinization, or lysis and deproteinization, are performed at the same time.

It is a further object of this invention to provide a reagent composition for neutralizing and deproteinating, or lysing and deproteinating, in a single step.

It is a further object of this invention to provide such a reagent composition which is stable at room temperature (approximately 25° C.) for at least thirty days.

This invention results from the realization that a reagent may be formulated for performing the lysis and deproteinization, or neutralization and deproteinization, at the same time in a single step. This invention results from the further realization that such a reagent composition is stable at room temperature for thirty days or more, providing for the automation of a separation method in which the lysis and deproteinization, or neutralization and deproteinization, is performed in a single step.

This invention features a stable single phase composition for isolating and purifying nucleic acid from cell culture medium and an improved method using such composition. The improved method includes performing at least some of the lysing and the deproteinating at the same time with a stable single phase aqueous composition. The composition includes about 1 to 3.5M acetate salt solution, about 4 to 11.2M acetic acid, about 1 to 40% by volume phenol, and about 1 to 40% by volume chloroform. The composition may further include 0 to about 2% by volume isoamyl alcohol and 0 to about 0.5% by weight hydroxyquinoline for further stabilizing the aqueous composition. For separation of double-stranded plasmid, phagmid, or cosmid DNA, the reagent performs the post-lysis neutralization and deproteinization at the same time. In situations in which neutralization is not needed, the aqueous composition may be used to perform substantially all of the lysing and the deproteinization at the same time. The method may be used for separating single- or double-stranded bacteriophage or cellular DNA; The bacteriophage may be M13 or lambda.

Preferably, the acetate salt in the aqueous composition is taken from the group including potassium, lithium, magnesium and sodium acetate. A preferred acetate salt is potassium acetate.

In a preferred embodiment, the single phase aqueous composition is stable against separation of phases for at least thirty days of storage at about 25° C., and includes about 1.5 to 2.9M potassium acetate, about 5 to 9.8M acetic acid, about 1.2 to 25% by volume phenol, and about 1.2 to 25% by volume chloroform. The composition may further include for increased stability no more than 0.5% by volume isoamyl alcohol and no more than 0.05% by weight 8-hydroxyquinoline.

The composition is remarkable in that it alters the solubility of phenol. Heretofore, the immiscibility of phenol with the lysing reagents dictated the necessity of performing the lysis in a first step and then the deproteinization in a second, separate step. With the composition of the present invention, those two steps may now be performed at the same time. It is believed that the composition of the novel reagent alters the ionic strength of the potassium acetate solution and makes the solution and the phenol miscible and stable indefinitely; over 60 days' room temperature storage has been observed.

The aqueous composition provides for automation of the separation procedure in that it has long-term stability and so may be used in automatic separation equipment in which reagents are stored and dispensed as necessary to perform the separation steps. In that case, a sealed package useful in an automated procedure for isolating DNA from cell cultures containing the disclosed stable single phase aqueous composition may be provided. Further, an improved nucleic acid isolation procedure in which cells and cell culture are lysed and nucleic acids are extracted from proteinaceous contaminants is provided in which the improvement includes employing the stable aqueous composition described.

The improved method of the present invention may be accomplished in the following steps:

First, the cells in the culture are concentrated apart from major contaminants in the media by centrifugation. Low- or high-speed centrifugation could be used throughout the protocol, with conditions readily determined by one skilled in the art. When employing this method for the isolation of template DNA, the bacteriophage can be separated from host bacterial cells by centrifugation, after which the baterial cells are pelleted while the bacteriophage remain in the liquid media. Another alternative is to isolate both plasmid DNA from the bacterial host cells and template DNA from the bacteriophage in the liquid media by concentrating the bacteriophage with an additional centrifugation step.

Next, the cells are lysed in the absence of lysozyme, and then deproteinated at room temperature (or ambient temperature) as follows: The cells are gently mixed in an isotonic buffer. One desirable buffer solution contains glucose, ethylene-diaminetetraacetic acid (EDTA) and Tris.Cl. After the first mixing, a salt and detergent solution (desirably sodium hydroxide and sodium dodecyl sulfate [SDS]) is added to the buffer and mixed to lyse the cells. Then, the novel reagent composition of this invention is added to neutralize and deproteinate at the same time. The composition also performs additional lysis. Selection of the particular isotonic buffer and the salt and detergent solution involve conventional choices for one of skill in this art.

Alternatively, for separation of single- or double-stranded bacteriophage or cellular (e.g. blood) DNA, the novel composition of this invention is added after the first mixing in the buffer. In that case, the composition performs the lysis and deproteinization at the same time; no neutralization is required.

After the lysis, neutralization and deproteinization, the cellular debris is eliminated from the solution of the second step by centrifugation. Then, the DNA is extracted by precipitation in an alcohol solution and concentrated by centrifugation at room temperature. The concentration may alternatively be accomplished by filtration.

Next, the concentrated DNA is washed to remove contaminants which otherwise might be co-purified with the DNA. The washing can be performed with a lower alkyl alcohol, such as ethanol. The washed DNA is then resuspended by incubation at room temperature in a low ionic strength buffer. Such a buffer may include RNase, Tris.Cl and EDTA. Other buffers are well known to those skilled in the art of DNA isolation techniques.

The long-term room-temperature stability of the composition of the present invention makes it convenient for use in isolating and purifying both single-stranded template DNA and double-stranded plasmid DNA. The present method also allows combination into one step of two steps of prior isolation techniques and thus greatly simplifies the isolation procedure. Unexpectedly, in practicing the method of the invention, an increased yield of DNA molecule isolation over the prior art procedures usually occurs, producing molecules of equal or greater purity. The yield increase has been postulated to be due to the extra lysis performed by the novel composition when it is used to neutralize and deproteinate.

DISCLOSURE OF PREFERRED EMBODIMENTS

Other objects, features and advantages will occur to those skilled in the art from the following description of preferred embodiments.

This invention may be accomplished in a stable single phase aqueous composition for use in isolating and purifying nucleic acid from cell culture medium, and an improved method using such composition. The composition is fully miscible and stable for at least thirty days at room temperature for long-term storage and use in automated separation procedures. The composition further performs at least some of the lysing and the deproteinating at the same time. For separation of double-stranded plasmid, phagmid or cosmid DNA, the composition performs the neutralization as well.

The stable composition may be accomplished with about 1 to 3.5M acetate salt solution, about 4 to 11.2M acetic acid, about 1 to 40% by volume phenol, and about 1 to 40% by volume chloroform. Up to 2% by volume isoamyl alcohol and up to 0.5% by weight hydroxyquinoline may be added to further stabilize the composition.

The method of this invention is capable of replacing a variety of standard DNA isolation procedures, including the isolation of DNA from eukaryotic and prokaryotic cell and virus cultures. The following examples illustrate preferred embodiments of the present invention, including the composition of the stable reagent and the improved method employing that reagent.

EXAMPLE I

Preparation of the Reagent Composition

The stable aqueous reagent composition of the invention may be prepared as follows:

In a first solution, 48 mls 5M potassium acetate is mixed with 32 mls glacial acetic acid. A second solution is formed by adding in the following order: 9.9 mls phenol, 0.1% by weight 8-hydroxyquinoline, 9.9 mls chloroform, and 0.2 mls isoamyl alcohol. These two solutions are mixed together, thereby forming a stable single phase composition. The reagent is stable from separation for at least thirty days at room temperature.

EXAMPLE II

Plasmid DNA Isolation from Bacterial Cells

One embodiment of the method of the present invention involves plasmid DNA isolation from bacterial cell culture, which may be performed as follows: 5 mls of SOBM medium [Maniatis et al., supra, p. 69] are inoculated with E. coli JM101 bacterial cells and M13mp19 bacteriophage and incubated overnight at 37° C. The cells are concentrated by centrifugation at a rate of 3000 rpm for 10 minutes. After the medium is poured off, the resulting pellet is resuspended in 0.3 mls of 50mM glucose, 10mM ethylenediamine-tetraacetic acid (EDTA), and 10mM tris-Cl at pH 7.5 and vortexed for 2 minutes at room temperature. Immediately following the vortex step, 0.6 mls of 0.2N NaOH and 1% SDS is added to denature and lyse the contents. The solution is vortexed gently at room temperature for 15 seconds, incubated for 30 seconds and vortexed gently again for 15 seconds.

To this solution, 0.54 mls of the composition of Example I is added. The composition neutralizes the solution, allowing renaturization, and deproteinates the sample in a single step; it also further completes the lysis. The mixture is gently vortexed for 15 seconds, incubated for 30 seconds, vortexed again for 15 seconds, and then centrifuged for 15 minutes at 3000 rpm.

The resulting supernatant is transferred to a test tube having a 0.8 micron pore size cellulose acetate filter and a 5 ml receiver tube [Schliecher and Schuell]. 1.3 mls isopropanol is added to the tube and it is vortexed gently, followed by a 2-minute room temperature incubation. To bind the DNA to the filter, the contents of the tube are centrifuged for 4 minutes at 3000 rpm at room temperature. While the DNA is on the filter, 0.5 mls of 70% ethanol is added to the tube and centrifuged again for 2 minutes. This step is repeated three more times to insure complete removal of the contaminants.

The receiver tube is then removed and replaced with a 1.5 ml capless Eppendorf tube. 0.1 ml of a reagent solution containing 10mM Tris-Cl at pH 8.0, mM EDTA and 20 ugs/ml RNase A is added to the tube and incubated for 5 to 30 minutes at room temperature to allow the DNA to be released from the filter. The tube and its contents are then centrifuged for 4 minutes at 3000 rpm at room temperature.

10ul of the resulting solution is placed in a new Eppendorf tube. 1.2ul of 10X EcoRI buffer is added with 1 unit of EcoRI New England Biolabs) restriction enzyme, and the resulting solution incubated for 2 hours at 37° C. The solution containing DNA fragments is analyzed by gel electrophoresis, producing linearized double-stranded plasmid DNA of 7.2 kb.

When the procedure described in Maniatis et al was applied to purify the same culture, the electrophoretic gel data produced the same results as did the above procedure employing the composition of the present invention. However, the time savings caused by use of the composition of the present invention to neutralize and deproteinate in a single step in the automated procedure was approximately 10-15 percent. Additionally, in both the manual and automated DNA plasmid isolation procedures, use of the composition of the present invention resulted in significantly higher yields of the isolated DNA fragments.

EXAMPLE III

Template DNA Isolation from Bacteriophage M13

Another embodiment of the claimed method involves isolating single-stranded template DNA. This procedure is exemplified as follows: The culture employed in Example II is subjected to the same low-speed centrifugation step. Thereafter, the liquid medium which contains the bacteriophage is transferred to a new tube containing 2 mls of 1.5M NaCl in polyethylene glycol [PEG, molecular weight of 8,000]. The pellet containing the bacterial cells is not used in this procedure. The two solutions are mixed in the tube by repeated pipetting motion and allowed to sit at room temperature (e.g., ambient temperature) for at least 30 minutes.

The bacteriophage are then separated from the solutions by low-speed centrifugation [3000 rpm] for 10 minutes, to enable them to be pelleted to the bottom of the tube. The supernatant is now discarded. The bacteriophage are resuspended by mixing in a 0.9 ml solution of glucose, EDTA and Tris-Cl, followed by the addition of 0.7 mls of the novel reagent of Example I. The solution is mixed to lyse and deproteinate in a single step. The bacteriophage debris is then eliminated from the solution by low-speed centrifugation.

The resulting supernatant is transferred to a test tube having a 0.8 micron pore size cellulose acetate filter and a 5 ml receiver tube [Schliecher and Schuell]. 1.3 mls isopropanol is added to the tube and it is vortexed gently, followed by a 2-minute room temperature incubation. To bind the DNA to the filter, the contents of the tube are centrifuged for 4 minutes at 3000 rpm at room temperature. While the DNA is on the filter, 0.5 nls at 70% ethanol is added to the tube and centrifuged again for 2 minutes. This step is repeated three more times to insure complete removal of contaminants.

The receiver tube is then removed and replaced with a 1.5 capless Eppendorf tube. 0.1 ml of a reagent solution containing 10 mM Tris-Cl at pH 8.0, 1 mM EDTA and 20 ugs/ml RNase A is added to the tube and incubated for 30 minutes at room temperature to allow the DNA to be released from the filter. The tube and its contents are then centrifuged for 4 minutes at 3000 rpm at room temperature 0.5 ul of the resulting solution was employed in the Sanger dideoxy sequencing protocol. The solution containing DNA fragments is analyzed by gel electrophoresis, producing linearized single-stranded M13 DNA.

When the procedure described in Maniatis et el was applied to purify the same cultures employed in this example, the electrophoretic gel data produced the same results as did the method of the present invention. However, the time savings caused by use of the method of the present invention was approximately 10-15 percent. Additionally, both the manual and automated DNA isolation procedures of the present invention resulted in significantly higher yields of the isolated DNA fragments.

Although one example of the preparation of the reagent composition of this invention was given along with two examples of the use of that composition in the method of this invention for isolating nucleic acid, this invention is not limited to that single composition or the disclosed methods. A stable single-phase aqueous composition useful in isolating nucleic acids may be accomplished by preparing a first solution of an acetate salt solution and acetic acid. Preferably, the acetate salt is potassium, lithium, magnesium or sodium acetate. The acetic acid is preferably glacial acetic acid.

A second solution is then prepared from phenol and chloroform. 8-hydroxyquinoline and isoamyl alcohol may be added to the second solution for further reagent stabilization and to decrease the amount of foaming on reagent mixing. The final solution has the components in the following concentrations: about 1 to 3.5M acetate salt, about 4 to 11.2M acetic acid, about 1 to 40% by volume phenol, and about 1 to 40% by volume chloroform. The isoamyl alcohol may be up to 2% by volume. The 8-hydroxyquinoline may be up to 0.5% by weight.

As described in Example I, 5M potassium acetate and glacial acetic acid may be employed to make the first solution. In that case, the volume ratio of the potassium acetate to acetic acid is preferably 3:2. In a preferred embodiment of the novel composition of this invention, the stable single phase composition has the following analysis: 2.4M potassium acetate, 7M acetic acid, 16.5% by volume phenol, 16.5% by volume chloroform, 0.33% by volume isoamyl alcohol, and 0.033% by weight 8-hydroxyquinoline.

The reagent of this invention may be used in techniques for separation of plasmid, cosmid or phagmid DNA to perform single step. The composition performs further lysing as well, which may increase the DNA yield. For isolation of other types of DNA, including bacteriophage and other cellular cultures (e.g. blood), no neutralization is necessary. In that case, the composition does the lysing and deproteinization at the same time in a single step. By the use of the composition of this invention, two steps of the DNA isolation procedure which have always been separately performed may now be performed in a single step, thereby saving a substantial amount of time by the elimination of an entire step.

The composition and method of this invention are well suited for an automated separation procedure because the composition is completely stable at room temperature for at least thirty days. The solutions may commonly be kept for sixty days or more. Because the automatic isolation procedures require volumes of the reagents to be prepared in advance and held, for example, in bottles for use in the procedure, in all known separation techniques the neutralization and deproteinating, or lysing and deproteinating, take place in two separate, distinct steps. The reason for the two-step procedure is that the reagents used for those steps were immiscible: a mixture of the two reagents would separate virtually immediately. The novel composition of the reagent according to this invention, however, provides the chemical components necessary to neutralize, lyse and deproteinate in a single reagent so that those isolation steps may take place at the same time. The resulting time and cost savings is apparent.

Although specific features of the invention have been described in some examples and not others, this is for convenience only as each feature may be combined with any or all of the other features in accordance with the invention.

Other embodiments will occur to those skilled in the art and are within the following claims:

What is claimed is:

1. A stable single phase aqueous composition useful in isolating nucleic acids from cell or virus cultures, comprising:
   about 1 to 3.5M acetate salt solution;
   about 4 to 11.2M acetic acid;
   about 1 to 40% by volume phenol; and
   about 1 to 40% by volume chloroform.

2. The composition of claim 1 further including no more than about 2% by volume isoamyl alcohol for further stabilizing said composition.

3. The composition of claim 2 in which there is no more than about 0.5% by volume isoamyl alcohol.

4. The composition of claim 1 further including no more than about 0.5% by weight hydroxyquinoline for further stabilizing said composition.

5. The composition of claim 4 in which the hydroxyquinoline is 8-hydroxyquinoline.

6. The composition of claim 5 in which there is no more than about 0.05% by weight 8-hydroxyquinoline.

7. The composition of claim 1 in which the acetate salt is taken from the group including potassium, lithium, magnesium and sodium acetate.

8. The composition of claim 7 in which the acetate salt is potassium acetate.

9. A sealed package useful in an automated procedure for isolating nucleic acid from cell cultures containing the stable single phase aqueous composition of claim 1.

10. In an improved nucleic acid isolation procedure in which cells in a cell culture are lysed and nucleic acids are extracted from proteinaceous contaminants, the improvement comprising employing the composition of claim 1.

11. A single phase aqueous composition that is stable against separation of phases for at least thirty days of storage at about 25 degrees Centigrade, and is useful in isolating nucleic acids from cell or virus cultures, comprising:
    about 1.5 to 2.9M potassium acetate;
    about 5 to 9.8M acetic acid;
    about 1.2 to 25% by volume phenol; and
    about 1.2 to 25% by volume chloroform.

12. The composition of claim 11 further including:
    0 to 0.5% by volume isoamyl alcohol; and
    0 to 0.05% by weight 8-hydroxyquinoline for further stabilizing said composition.

13. An improved method for isolating and purifying nucleic acid from cell culture media of the type in which:
    cells in the culture are concentrated apart from major contaminants in the media;
    the cells are lysed;
    the resulting solution is deproteinated;
    cellular debris is eliminated;
    the nucleic acid is extracted by precipitation;
    the nucleic acid is washed to remove contaminants; and
    the precipitated nucleic acid is resuspended;
    wherein the improvement comprises performing at least some of said lysing and said deproteinization at the same time with a stable single phase aqueous composition comprising:
    about 1 to 3.5M acetate salt solution;
    about 4 to 11.2M acetic acid;
    about 1 to 40% by volume phenol; and
    about 1 to 40% by volume chloroform.

14. The improved method of claim 13 in which said nucleic acid includes double-stranded plasmid, phagmid or cosmid DNA and the method includes a further step of neutralization after lysing, in which the improvement includes performing said neutralization and said deproteinization at the same time.

15. The improved method of claim 13 in which said nucleic acid includes single- or double-stranded bacteriophage or cellular DNA.

16. The improved method of claim 15 in which said bacteriophage includes M13 or lambda.

17. The improved method of claim 13 in which the improvement includes performing substantially all of said lysing and said deproteinization at the same time.

18. An improved method for isolating and purifying nucleic acid from cell culture media of the type in which:

cells in the culture are concentrated apart from major contaminants in the media;
the cells are lysed;
the resulting solution is neutralized and deproteinated;
cellular debris is eliminated;
the nucleic acid is extracted by precipitation;
the nucleic acid is washed to remove contaminants; and
the precipitated nucleic acid is resuspended;
wherein the improvement comprises performing said neutralization and said deproteinization at the same time with a stable single phase aqueous composition comprising:
about 1 to 3.5M acetate salt solution;
about 4 to 11.2M acetic acid;
about 1 to 40% by volume phenol; and
about 1 to 40% by volume chloroform.

* * * * *